(12) United States Patent
Liu et al.

(10) Patent No.: US 7,964,752 B2
(45) Date of Patent: Jun. 21, 2011

(54) BIFUNCTIONAL COMPOUND CONTAINING AMINO GROUP AND DIAMINEDITHIOL LIGAND AND MANUFACTURING METHOD THEREOF

(75) Inventors: Show-Wen Liu, Shetou Township, Changhua County (TW); Cheng-Hsien Lin, Taipei (TW); Tsyh-Lang Lin, Bade (TW); Cheng-Fang Hsu, Toufen Township, Miaoli County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 126 days.

(21) Appl. No.: 12/540,467

(22) Filed: Aug. 13, 2009

(65) Prior Publication Data

US 2011/0040123 A1 Feb. 17, 2011

(51) Int. Cl.
*C07C 233/05* (2006.01)
*C07C 237/10* (2006.01)

(52) U.S. Cl. .................................................. 564/154
(58) Field of Classification Search .................. 564/154
See application file for complete search history.

(56) References Cited

U.S. PATENT DOCUMENTS 4,279,805 A * 7/1981 Ohzeki et al. .................. 524/225
* cited by examiner

*Primary Examiner* — Shailendra Kumar
(74) *Attorney, Agent, or Firm* — Ming Chow; Sinorica, LLC

(57) ABSTRACT

A bifunctional compound containing an amino group and diaminedithiol ligand and a manufacturing method thereof are revealed, the bifunctional compound includes at least one amino group and a diaminedithiol ($N_2S_2$) ligand. The amino groups is for reacting with compounds containing carboxylic acids or halogens while the $N_2S_2$ ligand binds with technetium or rhenium so as to form an anion complex. The thiol group in the $N_2S_2$ ligand is protected by a protecting group for prevention of oxidation and easy storage. This protecting group is released easily during complex reactions. Due to the bifunctional property, the compound is applied to preparation of radiopharmaceuticals such as imaging agents and targeted agents.

9 Claims, 4 Drawing Sheets

BIFUNCTIONAL COMPOUND CONTAINING AMINO GROUP AND DIAMINEDITHIOL LIGAND AND MANUFACTURING METHOD THEREOF

BACKGROUND OF THE INVENTION

1. Field of Invention

The present invention relates to a bifunctional compound and a manufacturing method thereof, especially to a bifunctional compound containing an amino group and diaminedithiol ligand and a manufacturing method thereof.

2. Description of Related Art

Receptors on human cells are activated by certain kinds of specific compounds such as amines, amino acids, peptides or proteins. By means of such character, these bioactive compounds are labeled with radioactive nuclides. Once entering human bodies, these compounds will crowd toward specific organs or tissues so as to be applied to imaging diagnosis or disease treatment. For example, apoptosis is highly correlated with treatment of a plurality of diseases so that studies regarding radioactive labeled protein Annexin-V have received significant attention.

For direct labeling of proteins or peptides with radiometal isotopes such as Tc-99m, the two parts are tethered by means of a bifunctional ligand. S-Hynic (succinimidyl 6-hydrazinonicotinate hydrochloride) contains an active carboxylic ester that combines with proteins or peptides to generate a strong amide bond. Moreover, it includes pyridinyl and hydrazo groups that react with Tc-99m. Thus S-Hynic is a common bifunctional coupling agent. Furthermore, S-Hynic solution is light sensitive and light causes it to degrade. In addition, S-Hynic itself is unable to form sufficient bonds so that tricine is used as a coligand. Thus there is a need to find out a bifunctional compound (chelating agent) that is with stable physical properties and easy to use.

DADT (diamide dithiol) and BAT (bis-aminoethanethiol) are frequently used organic ligands that bind with technetium (Tc) or rhenium (Re) to form complexes (coordination compounds). As shown in FIG. 1, the representative structure of DADT as well as BAT and their complex reactions with Tc or Re are illustrated. While reacting with $MO^{3+}$ (M=Tc or Re), four protons are released from two amide groups and two thiol groups of DADT. Thus the DADT complex is an anion. When BAT reacts with $MO^{3+}$ (M=Tc or Re), only three protons are released and the complex is electrically neutral.

The thiol group is easily oxidized so that it must be protected. The common protecting groups include $COC_6H_5$, $CH_2C_6H_4OCH_3$ and $CPh_3$ etc. Before complex reaction, the protecting group for the thiol group must be removed. For example, $COC_6H_5$ is used as a protecting group for the $MAG_3$. Thus the $MAG_3$ is hydrolyzed in alkaline solution so as to remove the protecting group before the complex reaction.

In accordance with above description, a $N_2S_2$ ligand having two amide groups and two thiol groups reacts with $MO^{3+}$ (M=Tc or Re) to form a complex anion. Then an amino group is added to this type of ligand so that the ligand reacts with compounds containing carboxylic acids or halogens to form chemical bonds and generate a bifunctional compound. Moreover, $CPh_3$ is used as the protecting group for the thiol group in the present invention. The protecting group ($CPh_3$) is released easily during the complex reaction and there is no need to remove the protecting group in advance. This allows convenient use of the bifunctional compound.

SUMMARY OF THE INVENTION

Therefore it is a primary object of the present invention to provide a bifunctional compound containing an amino group and diaminedithiol ligand and a manufacturing method thereof. The bifunctional compound containing an amino group and diaminedithiol ligand not only reacts with carboxylic acids and halogens but also binds with $TcO^{3+}$ or $ReO^{3+}$ so as to be applied to preparation of Tc-labeled or Re-labeled radiopharmaceuticals.

It is another object of the present invention to provide a bifunctional compound containing an amino group and diaminedithiol ligand and a manufacturing method thereof in which $CPh_3$ is used as a protecting group for the thiol group. This protecting group is released easily during the complex reactions and there is no need to remove the protecting group in advance. Thus the bifunctional compound can be used in a more convenient way.

In order to achieve above objects, the present invention provides a bifunctional compound containing an amino group and diaminedithiol ligand and a manufacturing method thereof. The bifunctional compound can bind with compounds containing carboxylic acids or halogens and Tc/or Re at the same time to form radiopharmaceuticals for disease diagnoses or targeted agents.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In conventional techniques, a protecting group such as COC6H5, CH2C6H4OCH3 and CPh3 etc. is used for protection of the thiol group that is easily oxidized. The protecting group must be removed before the complex reaction. In the present invention, CPh3 is used as the protecting group for the thiol group and is released during the complex reaction. Thus there is no need to remove this protecting group by additional processes in advance. The bifunctional compound can be used in a more convenient way.

The present invention discloses a bifunctional compound containing an amino group and diaminedithiol ligand as followings:

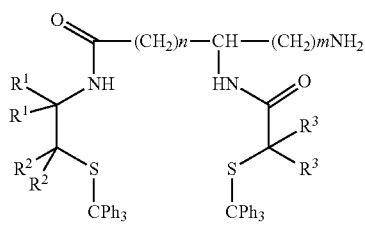

Wherein R1=H or CH3, R2=H or CH3, R3=H or CH3, n=0~3, m=1~18. Furthermore, the compound is L-Nε-[2-(Triphenylmethyl)thioacetyl]-6-aza-5-oxo-9-(triphenylmethyl)-thio-1,5-nonanediamine (NODA) when R1=R2=R3=H, n=0 and m=4.

Figure 1:
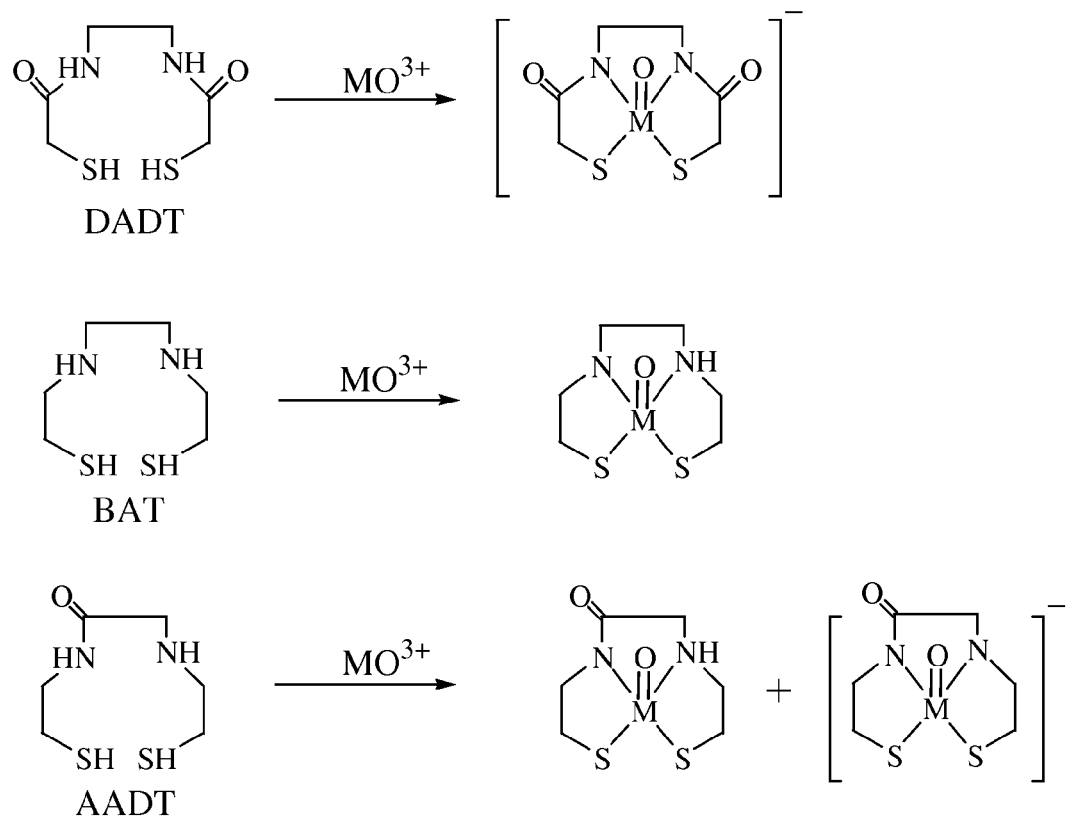
FIG. 1 shows conventional compounds having $N_2S_2$ ligand and their complexes (M=Tc or Re)
Figure 2A:
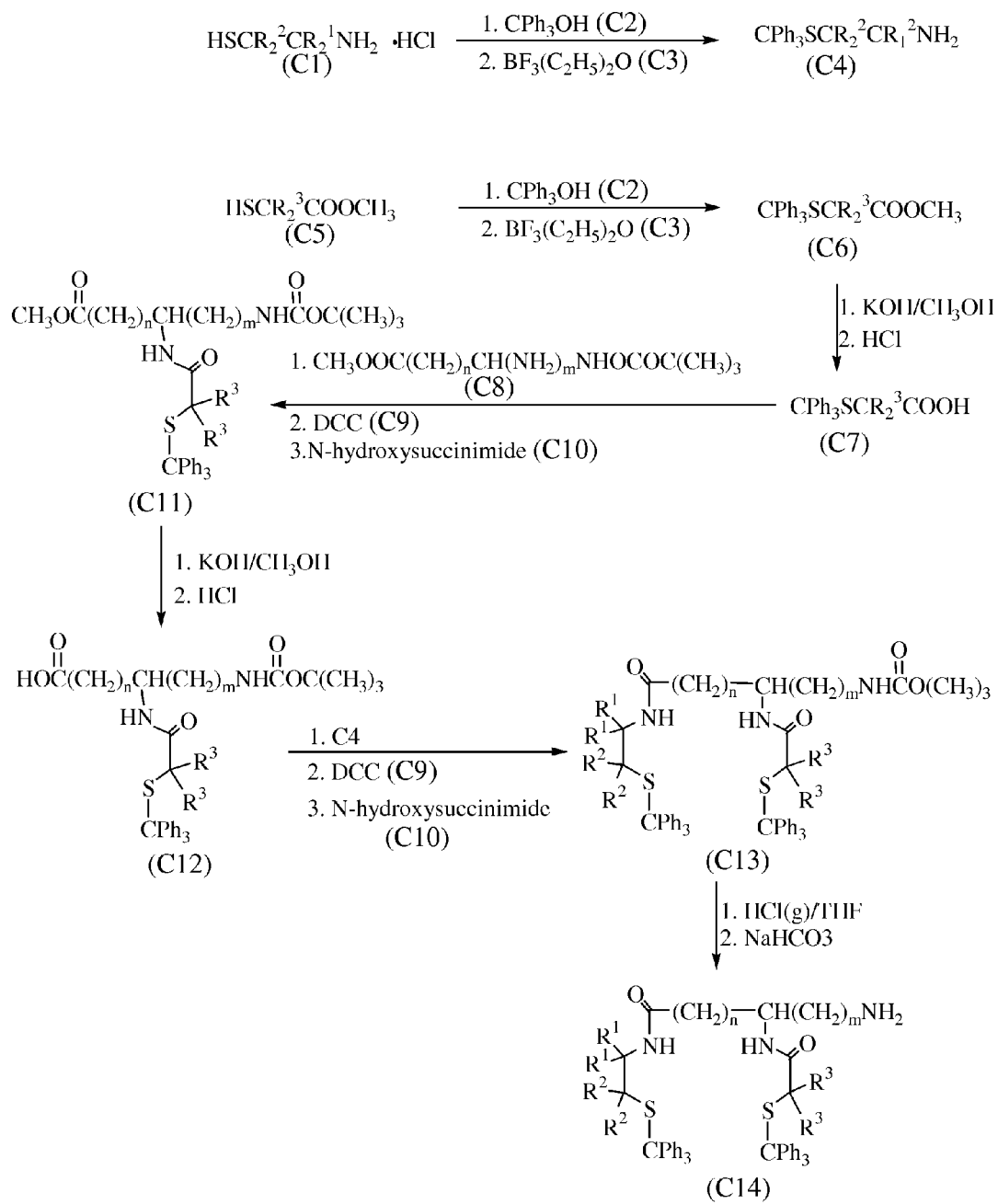
FIG. 2A shows reaction equations of an embodiment according to the present invention.
Figure 2B:
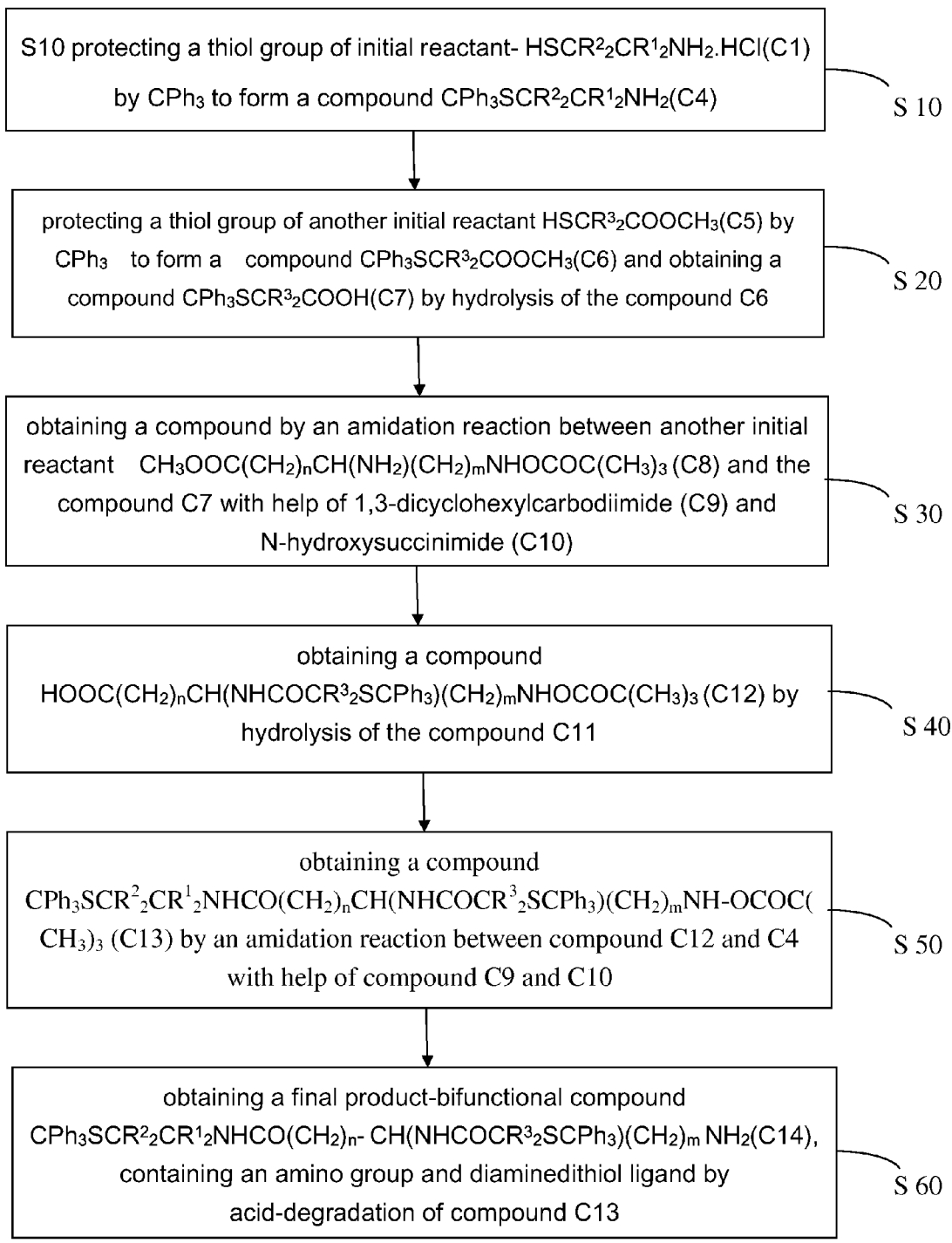
FIG. 2B is a flow chart showing manufacturing processes of an embodiment of NODA according to the present invention.
Figure 2C:
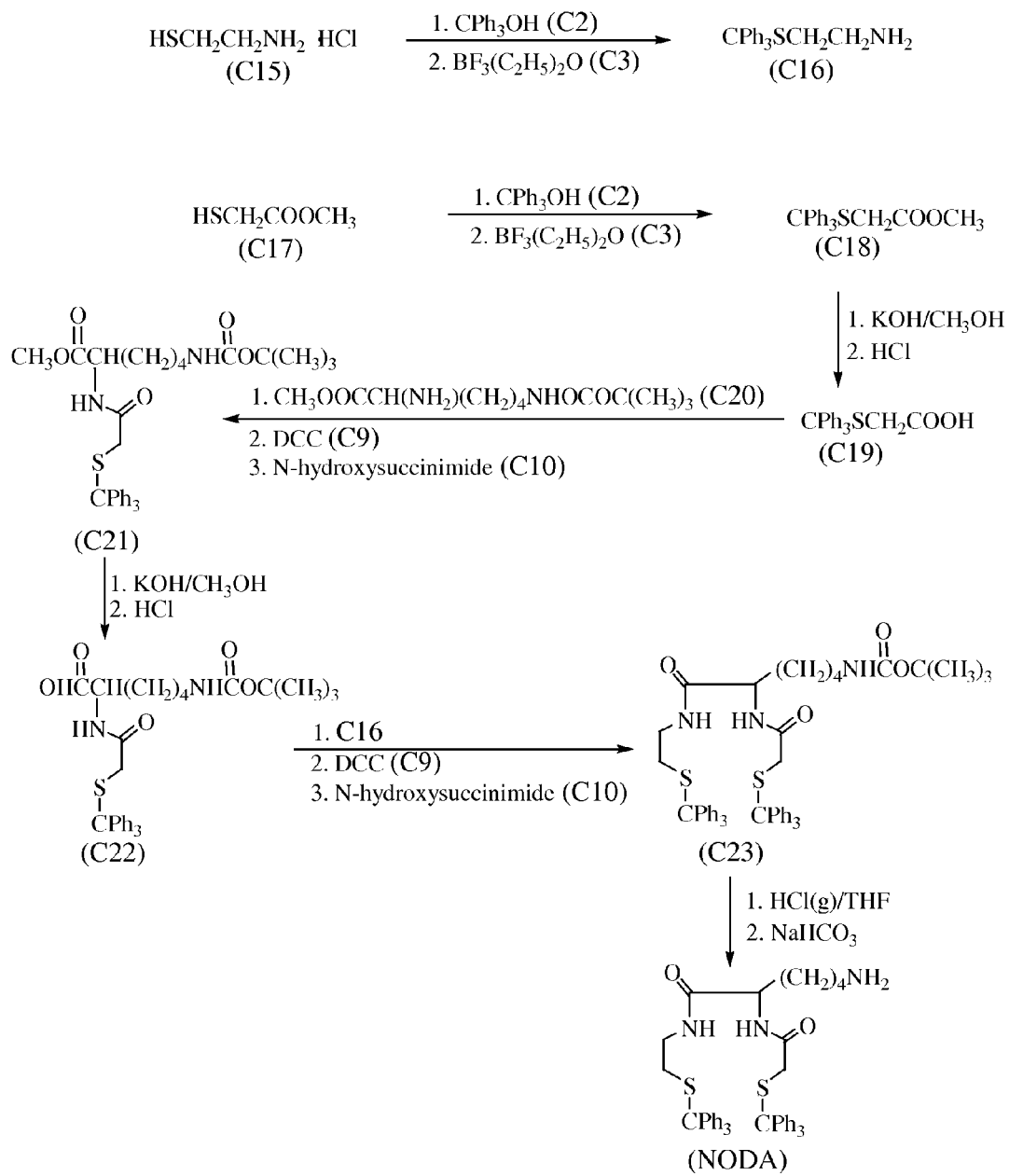
FIG. 2C shows reaction equations of an embodiment of NODA according to the present invention.

Refer to FIG. 2A, FIG. 2B and FIG. 2C, reaction equations and a flow chart of an embodiment according to the present invention are revealed. As shown in figures, a manufacturing method of a bifunctional compound containing an amino group and diaminedithiol ligand includes the following steps:

Step S10 protecting a thiol group of initial reactant-$HSCR^2_2CR^1_2NH_2 \cdot HCl(C1)$ by $CPh_3$ to form a compound $CPh_3SCR^2_2CR^1_2NH_2(C4)$;

Step S20 protecting a thiol group of another initial reactant $HSCR^3_2COOCH_3(C5)$ by $CPh_3$ to form a compound $CPh_3SCR^3_2COOCH_3(C6)$ and obtaining a compound $CPh_3SCR^3_2COOH(C7)$ by hydrolysis of the compound C6;

Step S30 obtaining a compound CH3OOC(CH2)nCH(NHCOCR32SCPh3)(CH2)mNHOCOC(CH 3)3 (C11) by an amidation reaction between another initial reactant CH3OOC(CH2)nCH(NH2)(CH2)mNHOCOC(CH3)3 (C8) and the compound C7 with help of 1,3-dicyclohexylcarbodiimide (C9) and N-hydroxysuccinimide (C10);

Step S40 obtaining a compound $HOOC(CH_2)_nCH(NHCOCR^3_2SCPh_3)(CH_2)_mNHOCOC(CH_3)_3$ (C12) by hydrolysis of the compound C11;

Step S50 obtaining a compound $CPh_3SCR^2_2CR^1_2NHCO(CH_2)_nCH(NHCOCR^3_2SCPh_3)(CH_2)_mNH-OCOC(CH_3)_3$ (C13) by an amidation reaction between compound C12 and C4 with help of compound C9 and C10;

Step S60 obtaining a final product-bifunctional compound $CPh_3SCR^2_2CR^1_2NHCO(CH_2)_nCH(NHCOCR^3_2SCPh_3)(CH_2)_m NH_2(C14)$, containing an amino group and diaminedithiol ligand by acid-degradation of compound C13.

Use the following bifunctional compound-L-Nε-[2-(Triphenylmethyl)thioacetyl]-6-aza-5-oxo-9-(triphenylmethyl)-thio-1,5-nonanediamine (NODA) as an embodiment of the present invention.

Refer to FIG. 2C, a chart showing manufacturing processes of NODA according to the present invention is revealed. As shown in figure, firstly, synthesize the compound 2-[(Triphenylmethyl)thio]ethylamine (C16). Dissolve 10 g (88.4 mmol) compound 2-thioethylamine hydrochloride (C15), 22 g (85 mmol) triphenylmethanol (C2) and 14 mL (99.7 mmol) triethylamine in 100 mL chloroform. Then heat under reflux at 75 degrees Celsius and a catalyst 30 mL (239 mmol) borontrifluoride ethyl ether complex (C3) is slowly dropped into the mixture. Then continue heating under reflux for 4 hours. The solution is decompressed and condensed. Add methanol to dissolve and then the solution is condensed again. Next add sodium bicarbonate solution and stir the solution until a white precipitate forms. Then vacuum filter to obtain the precipitate (solid). After washing with water and drying, a solid product-compound C16 (27.9 g, 99%) is obtained.

Analysis of the synthesis product: IR (neat) ν 3381 ($NH_2$) $cm^{-1}$. $^1H$ NMR ($CDCl_3$) δ 7.42 (m, 3 H, Ph), 7.30 (m, 12 H, Ph), 2.58 (t, J=6.6 Hz, 2 H, $CH_2N$), 2.32 (t, J=6.6 Hz, 2 H, $CH_2S$), 1.45 (br, 2 H, $NH_2$). $^{13}C$ NMR ($CDCl_3$) δ 144.80, 192.52, 127.81 and 126.60 (Ph), 66.51 (CPh), 40.94 ($CH_2N$), 36.09 ($CH_2S$). MS m/z 319 ($M^+$), 243 ($M^+$-$C_6H_5$+1).

Moreover, synthesize of triphenylmethyl thioglycolic acid methyl ester (C18). Dissolve 5.0 ml (55.0 mmol) methyl thioglycolate (C17), 14.3 g (55.0 mmol) triphenylmethanol (C2) in 80 mL chloroform. 6.9 mL (55.0 mmol) borontrifluoride ethyl ether complex (C3) is slowly dropped into the mixture and is stirred at room temperature. Use thin-layer chromatography (TLC) (chloroform:hexane=1:1) to monitor the progress of the reaction. After disappearing of initial material, wash the reaction solution with water (2×100 mL). The organic phase is dried over anhydrous sodium sulfate, then decompressed and evaporated (dried out) to get a product-compound C18 (18.6 g, 97.5%).

Analysis of the synthesis product: IR (neat) ν 1739 (CO) $cm^{-1}$. $^1H$ NMR ($CDCl_3$) δ 7.43-7.21 (m, 15 H, Ph), 3.56 (s, 3 H, $CH_3$), 2.98 (s, 2 H, $CH_2$). $^{13}C$ NMR ($CDCl_3$) δ 169.97 (CO), 143.93, 129.47, 127.99 and 126.83 (Ph), 67.01 ($CPh_3$), 52.30 ($CH_3$), 34.43 ($CH_2$). MS m/z 243 (($CPh_3$)$^+$)$_o$ Synthesis of Triphenylmethyl thioglycolic Acid (C19)

Take 18.6 g (53.5 mmol) compound C18 into a 300 mL solution of potassium hydroxide in methanol (10%) and stir the solution until the compound C18 dissolves completely. After decompression and condensation, dissolve the residue with 100 mL 50% aqueous ethanol solution and drop concentrated hydrochloric acid into the solution until the PH is 6. Use chloroform (3×100 mL) to extract. The organic phase is dried over anhydrous sodium sulfate, then decompressed and evaporated for removing solvent so as to obtain a product-compound C19 (17.9 g, ~100%).

Analysis of the synthesis product: IR (KBr) ν 3447 (OH), 1705 (CO) $cm^{-1}$. $^1H$ NMR ($CDCl_3$) δ 7.45-7.19 (m, 15 H, Ph), 2.97 (s, 2 H, $CH_2$). $^{13}C$ NMR ($CDCl_3$) δ 175.27 (CO), 144.0, 129.46, 128.03 and 126.84 (Ph), 66.91 ($CPh_3$), 53.11 ($CH_2$). $^{13}C$ NMR ($CDCl_3$) δ 175.27 (CO), 144.0, 129.46, 128.03 and 126.84 (Ph), 66.91 (CPh), 53.11 ($CH_2$). MS m/z 243 (($CPh_3$)$^+$)$_o$ Synthesis of L-Nε-tert-Butoxycarbonyl-Nα-[2-(triphenylmethyl)thioacetyl]lysine methyl ester (C21)

Dissolve 4.50 g (15.2 mmol) L-Nε-tert-butoxycarbonyll-ysine methyl ester hydrochloride (C20), 4.70 g (22.8 mmol) 1,3-dicyclohexylcarbodiimide (C9), 2.10 g (18.2 mmol) N-hydroxysuccinimide (C10), 5.07 g (15.2 mmol) triphenylmethyl thioglycolic acid, and 6.3 ml (45.6 mmol) triethylamine in 80 mL chloroform and heat at 50 degrees Celsius overnight. Filter the solution to remove solid and the filtrate is decompressed and evaporated. Add 50 mL acetone to dissolve the residue, filter the solution, and the filtrate is decompressed and evaporated. By a technique of separation and purification-liquid chromatography ($SiO_2$, $CHCl_3$:EtOAc=4:1), a solid product-compound C21 (4.91 g, 56%) is obtained.

Analysis of the synthesis product: IR (KBr) ν 3337 (NH), 1742 and 1669 (CO) $cm^{-1}$. $^1H$ NMR ($CDCl_3$) δ 7.39-7.17 (m, 15 H, Ph), 6.51 (d, J=7.5 Hz, 1 H, NHCH), 4.51 (br, 1 H, $NHCH_2$), 4.30 (q, J=6.0 Hz, 1 H, NCH), 3.69 (s, 3 H, $OCH_3$), 3.06 (s, 2 H, $CH_2S$), 3.02 (m, 2 H, $CH_2N$), 1.65 (m, 2 H, $CHCH_2$), 1.50 (m, 2 H, $CH_2CH_2NH$), 1.40 (s, 9 H, $C(CH_3)_3$), 1.68 (m, 2 H, $CH_2CH_2CH$). $^{13}C$ NMR ($CDCl_3$) δ 172.23, 167.88 and 155.90 (CO), 143.95, 192.51, 128.09 and 127.0 (Ph), 77.18 ($C(CH_3)_3$), 67.93 ($CPh_3$), 52.27 and 52.15 ($CH_3O$ and CH), 40.15 ($CH_2NH$), 36.06, 32.01, 29.47 and 22.29 ($CH_2$), 28.37 ($C(CH_3)_3$)$_o$ Synthesis of L-Nε-tert-Butoxycarbonyl-Nα-[2-(triphenylmethyl)thioacetyl]lysine (C22)

Dissolve 4.91 g (8.5 mmol) compound C21 in into a 80 ml solution of potassium hydroxide in methanol (10%) and stir the solution for 30 minutes. After being cooled in an ice-bath, add 30 mL water and drop concentrated hydrochloric acid into the solution until the PH is 6. Use dichloromethane to extract (3×80 ml). The organic phase is dried over anhydrous sodium sulfate, then decompressed and evaporated to obtain a solid product-compound C22 (4.80 g, 100%).

Analysis of the synthesis product: IR (KBr) ν 3348 (NH), 1714 and 1659 (CO) cm$^{-1}$. $^1$H NMR (DMSO-d6) δ 8.24 (d, J=7.8 Hz, 1 H, NHCH), 7.43-7.28 (m, 15 H, Ph), 6.80 (br, 1 H, NHCH$_2$), 4.12 (m, 1 H, CH), 2.92 (m, 4 H, CH$_2$S and CH$_2$NH), 1.69-1.20 (m, 6 H, CH$_2$CH$_2$CH$_2$CH), 1.41 (s, 9 H, C(CH$_3$)$_3$). $^{13}$C NMR (DMSO-d6) δ 173.28, 167.37 and 155.52 (CO), 144.08, 129.06, 128.05 and 126.76, (Ph), 77.29 (C(CH$_3$)$_3$), 65.91 (CPh$_3$), 52.10 (CH), 39.23, 35.74, 30.58, 29.05 and 22.68 (CH$_2$), 28.23 (CH$_3$)$_o$

Synthesis of [L-Nε-tert-Butoxycarbonyl-Nα-[2-(triphenylmethyl)thioacetyl]-6-aza-5-oxo-9-(triphenylmethyl)thio-1,5-nonanediamine (C23)

Dissolve 4.19 g (7.40 mmol) compound C22, 2.30 g (11.2 mmol) 1,3-dicyclohexylcarbodiimide (C9), 1.03 g (8.9 mmol) N-hydroxysuccinimide (C10), 2.38 g (7.4 mmol) 2-[(triphenylmethyl)thio]ethylamine (C16), and 3.1 mL (22.3 mmol) triethyamine in 100 mL chloroform and heat at 50 degrees Celsius overnight. Filter the solution and the filtrate is decompressed and evaporated. Add 100 mL acetone to dissolve residues, filter the solution, and the filtrate is decompressed and evaporated. By a technique of separation and purification-liquid chromatography (SiO$_2$, CHCl$_3$: CH$_3$OH=95:5), a product-compound C23 (3.1 g, 48%) is obtained.

Analysis of the synthesis product: IR (neat) ν 3290 (NH), 1688 and 1642 (CO) cm$^{-1}$. $^1$H NMR (CDCl$_3$) δ 7.40-7.16 (m, 30 H, Ph), 6.36 (d, J=7.8 Hz, 1 H, NHCH), 6.05 (br, 1 H, NH(CH$_2$)$_2$S), 4.55 (br, 1 H, NH(CH$_2$)$_4$), 4.02 (q, J=7.2 Hz, 1 H, CHNH), 3.03 (m, 6 H, CH$_2$CH$_2$S, COCH$_2$S and NHCH$_2$(CH$_2$)$_3$), 2.36 (t, J=6.6 Hz, 2 H, CH$_2$CH$_2$S), 1.78-1.13 (m, 6 H, (CH$_2$)$_3$CH), 1.42 (s, 9 H, C(CH$_3$)$_3$). $^{13}$C NMR (CDCl$_3$) δ 170.53, 168.20 and 155.87 (CO), 144.49, 143.87, 129.41, 128.06, 127.87, 126.96 and 126.69 (Ph), 77.13 (C(CH$_3$)$_3$), 67.86 and 66.72 (CPh$_3$), 52.98 (CH), 40.06, 38.17, 36.0, 31.68, 31.55, 29.47 and 22.50 (CH$_2$), 28.33 (C(CH$_3$)$_3$)$_o$

Synthesis of L-Nε-[2-(Triphenylmethyl)thioacetyl]-6-aza-5-oxo-9-(triphenyl methyl)thio-1,5-nonanediamine (NODA)

Dissolve 1.87 g (2.16 mmol) compound C23 in anhydrous tetrahydrofuran (THF), introduce hydrogen chloride gas into the solution and stir the solution at room temperature for 1 hour. Then the solution is filtered, decompressed and evaporated. Wash with 30 mL diethyl ether. Take the insoluble substance and the organic phase is washed by saturated sodium bicarbonate solution (30 mL). Next the organic phase is dried over anhydrous sodium sulfate, then decompressed and evaporated. At last, by a technique of separation and purification-liquid chromatography (SiO$_2$, CHCl$_3$: CH$_3$OH=70:30), the NODA (0.91 g, 55%) is obtained.

Analysis of the synthesis product: IR (neat) ν 3287 (NH), 1644 (CO) cm$^{-1}$. $^1$H NMR (CDCl$_3$) δ 7.41-7.17 (m, 30 H, Ph), 6.52 (d, J=7.8 Hz, NHCH), 6.45 (t, J=5.4 Hz, 1 H, NHCH$_2$), 4.07 (q, J=7.5 Hz, 1 H, CHNH), 3.01 (m, 4 H, CH$_2$CH$_2$S and CH$_2$S), 2.63 (t, J=6.6 Hz, 2 H, CH$_2$NH$_2$), 2.37 (m, 2 H, CH$_2$CH$_2$S), 1.92 (br, 2 H, NH$_2$), 1.67-1.18 (m, 6 H, (CH$_2$)$_3$CH). $^{13}$C NMR (CDCl$_3$) δ 170.71 and 168.20 (CO), 144.57, 143.94, 129.47, 128.09, 127.92, 126.99 and 126.74 (Ph), 67.85 and 66.74 (CPh$_3$), 53.07 (CH), 41.44, 38.23, 36.13, 32.46, 32.01, 31.65 and 22.49 (CH2)$_o$ In summary, the present invention has the following advantages:
1. The bifunctional compound containing an amino group and diaminedithiol ligand (C14) of the present invention includes an amino group to react with compounds containing carboxylic acids or halogens.
2. The bifunctional compound containing an amino group and diaminedithiol ligand (C14) of the present invention provides a N$_2$S$_2$ ligand that binds with technetium (Tc) or rhenium (Re) to be applied to nuclear medicines.
3. The compound formed by bonding of the bifunctional compound containing an amino group and diaminedithiol ligand (C14) of the present invention with Tc or Re is an anion complex. Compared with general neutral Tc or Re complex, it's more hydrophilic and is more optimal for preparation of radiopharmaceuticals.
4. The thiol group in the bifunctional compound containing an amino group and diaminedithiol ligand (C14) of the present invention is protected by CPh3 group so that its chemical property is stable and is easy for storage.
5. CPh$_3$ is used as the protecting group for the thiol group in the present invention. The protecting group (CPh$_3$) is released easily during the complex reaction with Tc or Re and there is no need to remove the protecting group in advance.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:
1. A bifunctional compound containing an amino group and diaminedithiol ligand comprising:

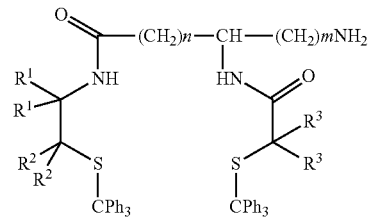

wherein R$^1$=H or CH$_3$, R$^2$=H or CH$_3$, R$^3$=H or CH$_3$, n=0~3, and m=1~18.

2. The compound as claimed in claim 1, wherein the compound is L-Nε-[2-(Triphenylmethyl)thioacetyl]-6-aza-5-oxo-9-(triphenylmethyl)-thio-1,5-nonanediamine (NODA) when R$^1$=R$^2$=R$^3$=H, n=0 and m=4.

3. A manufacturing method of a bifunctional compound containing an amino group and diaminedithiol ligand comprising the steps of:
protecting a thiol group of HSCR$^3$$_2$COOCH$_3$ by CPh$_3$ to form CPh$_3$SCR$^3$$_2$COOCH$_3$ and obtaining CPh$_3$SCR$^3$$_2$COOH by hydrolysis of CPh$_3$SCR$^3$$_2$COOCH$_3$;
obtaining CH$_3$OOC(CH$_2$)$_n$CH(NHCOCR$^3$$_2$SCPh$_3$)(CH$_2$)$_m$ NHOCOC(CH$_3$)$_3$ by an amidation reaction between CH$_3$OOC(CH$_2$)$_n$CH(NH$_2$)(CH$_2$)$_m$NHOCOC(CH$_3$)$_3$ and CPh$_3$SCR$^3$$_2$COOH with help of 1,3-dicyclohexylcarbodiimide and N-hydroxysuccinimide, obtaining $HOOC(CH_2)_nCH(NHCOCR^3{}_2SCPh_3)(CH_2)_mNHOCOC(CH_3)_3$ by hydrolysis of $CH_3OOC(CH_2)_nCH(NHCOCR^3{}_2SCPh_3)(CH_2)_mNHOCOC(CH_3)_3$; and obtaining $CPh_3SCR^2{}_2CR^1{}_2NHCO(CH_2)_nCH(NHCOCR^3{}_2SCPh_3)(CH_2)_mNHOCOC(CH_3)_3$ by an amidation reaction between $HOOC(CH_2)_n-CH(NHCOCR^3{}_2SCPh_3)(CH_2)_mNHOCOC(CH_3)_3$ and $CPh_3SCR^2{}_2CR^1{}_2NH_2$ with help of 1,3-dicyclohexylcarbodiimide and N-hydroxysuccinimide while $CPh_3SCR^2{}_2CR^1{}_2NH_2$ is formed by $HSCR^2{}_2CR^1{}_2NH_2 \cdot HCl$ in which the thiol group is protected by $CPh_3$, and obtaining a final product-bifunctional compound $CPh_3SCR^2{}_2CR^1{}_2NHCO(CH_2)_n-CH(NHCOCR^3{}_2SCPh_3)(CH_2)_mNH_2$ containing an amino group and diaminedithiol ligand by acid-degradation of $CPh_3SCR^2{}_2CR^1{}_2NHCO(CH_2)_nCH(NHCOCR^3{}_2SCPh_3)(CH_2)_mNHOCOC(CH_3)_3$.

4. The method as claimed in claim 3, wherein in the step of protecting a thiol group of $HSCR^3{}_2COOCH_3$ by $CPh_3$, triphenylmethanol is a reactant and boron trifluoride-diethyl ether complex ($BF_3 \cdot OEt_2$) is used as a catalyst.

5. The method as claimed in claim 3, wherein in the step of forming $CPh_3SCR^2{}_2CR^1{}_2NH_2$ by $HSCR^2{}_2CR^1{}_2NH_2 \cdot HCl$ in which the thiol group is protected by $CPh_3$, triphenylmethanol is a reactant and boron trifluoride-diethyl ether complex ($BF_3 \cdot OEt_2$) is used as a catalyst.

6. The method as claimed in claim 3, wherein in the step of protecting a thiol group of $HSCR^3{}_2COOCH_3$ by $CPh_3$ to form $CPh_3SCR^3{}_2COOCH_3$ and obtaining $CPh_3SCR^3{}_2COOH$ by hydrolysis of $CPh_3SCR^3{}_2COOCH_3$, hydrolysis is in methanol solution and potassium hydroxide or sodium methoxide is used as a catalyst.

7. The method as claimed in claim 3, wherein in the step of hydrolysis of $CH_3OOC(CH_2)_nCH(NHCOCR^3{}_2SCPh_3)(CH_2)_mNHOCOC(CH_3)_3$, hydrolysis is in methanol solution and potassium hydroxide or sodium methoxide is used as a catalyst.

8. The method as claimed in claim 3, wherein in the step of acid-degradation of $CPh_3SCR^2{}_2CR^1{}_2NHCO(CH_2)_n-CH(NHCOCR^3{}_2SCPh_3)(CH_2)_mNHOCOC(CH_3)_3$, the acid-degradation is in an organic solvent and hydrogen chloride or trifluoroacetic acid is a catalyst.

9. The method as claimed in claim 8, wherein the organic solvent is tetrahydrofuran (THF).

* * * * *